US005382654A

United States Patent [19]

Lyle et al.

[11] Patent Number: 5,382,654

[45] Date of Patent: Jan. 17, 1995

[54] RADIOLABELLED PEPTIDE COMPOUNDS

[75] Inventors: Leon R. Lyle, Webster Groves; Raghavan Rajagopalan; Karen Deutsch, both of Maryland Heights, all of Mo.

[73] Assignee: Mallinckrodt Medical, Inc., St. Louis, Mo.

[21] Appl. No.: 831,724

[22] Filed: Feb. 5, 1992

[51] Int. Cl.[6] ........................ C07K 7/26; A61K 43/00; A61K 49/02

[52] U.S. Cl. ........................ 530/311; 534/10; 534/14

[58] Field of Search ........................ 424/1.1, 1.45, 1.69; 530/311, 300; 930/22, 44

[56] References Cited

U.S. PATENT DOCUMENTS 5,225,180 7/1993 Dean et al. ........................ 424/1.1

FOREIGN PATENT DOCUMENTS 2225579 6/1990 United Kingdom .
9205154 4/1992 WIPO .
9221383 12/1992 WIPO .

OTHER PUBLICATIONS

*J. Nucl. Med.*, vol. 32, No. 5 (May 1991) Kwekkeboom et al., Abstract No. 305 "[In-111-DTPA-D-Phe]-Octreotide . . . ".

*J. Nucl. Med.*, vol. 31 (1990) Albert et al., Abstract LMIO, "A Somatostatin Analogue to Image-S-S-Receptor-Positive-Tumours . . . ".

Paper, *7th Int'l Symposium on Radiopharmacology* (1991) Cox et al. "*Technetium Labeled Somatostatin . . .* ".

*J. Nucl. Med.*, vol. 32, No. 6 (Jun. 1991) Bakker et al., "In Vivo Use of Radioiodinated Somatostatin Analogue", pp. 1184–1188.

*J. Nucl. Med.*, vol. 32, No. 6 (Jun. 1991) Larson, Receptors on Tumors Studied . . . , pp. 1189–1191.

*J. Nucl. Med.*, vol. 31, No. 9 (Sep. 1990) Bakker et al., "Receptor Scintigraphy with a Radioiodinated Somatostatin Analogue", pp. 1501–1509.

*J. Nucl. Med.*, vol. 32, No. 10 (Oct. 1991) Kwekkeboom et al., "Radioiodinated Somatostatin Analogue Scintigraphy . . . ", pp. 1845–1848.

*Primary Examiner*—Robert L. Stoll
*Assistant Examiner*—John M. Covert
*Attorney, Agent, or Firm*—Rita D. Vacca

[57] ABSTRACT

A diagnostic composition suitable for administration to a warm-blooded animal comprising somatostatin or a molecule capable of interacting with the somatostatin receptor labeled with a radionuclide by means of a chelate ligand capable of administration to an animal to produce reliable visual imaging of tumors or therapeutic effects on tumors.

8 Claims, No Drawings

RADIOLABELLED PEPTIDE COMPOUNDS

FIELD OF THE INVENTION

This invention relates generally to novel compounds for use in diagnostic tissue imaging and more particularly, to site specific radiolabelled peptides, to methods of preparing such site specific radiolabelled peptides, and to pharmaceutical compositions comprising these site specific radiolabelled peptides for diagnostic imaging or therapeutic use.

BACKGROUND OF THE INVENTION

Scintigraphic imaging and similar radiographic techniques for visualizing tissues in vivo are finding ever-increasing application in biological and medical research and in diagnostic and therapeutic procedures. Generally, scintigraphic procedures involve the preparation of radioactive agents which, upon introduction to a biological subject, become localized in the specific organ, tissue or skeletal structure of choice. When so localized, traces, plots or scintiphotos depicting the in vivo distribution of radiographic material can be made by various radiation detectors, e.g., traversing scanners and scintillation cameras. The distribution and corresponding relative intensity of the detected radioactive material not only indicates the space occupied by the targeted tissue, but also indicates a presence of receptors, antigens, aberrations, pathological conditions, and the like.

In general, depending on the type of radionuclide and the target organ or tissue of interest, the compositions comprise a radionuclide, a carrier agent designed to target the specific organ or tissue site, various auxiliary agents which affix the radionuclide to the carrier, water or other delivery vehicles suitable for injection into, or aspiration by, the patient, such as physiological buffers, salts, and the like. The carrier agent attaches or complexes the radionuclide to the peptide carrier agent, which results in localizing the radionuclide being deposited in the location where the carrier agent concentrates in the biological subject.

Technetium-99m($^{99m}$Tc) is a radionuclide which is widely known for its uses in tissue imaging agents. Due to its safety and ideal imaging properties, this radionuclide is conveniently available commercially in the oxidized pertechnetate form ($^{99m}TcO_4^-$) hereinafter "pertechnetate-Tc99m". However, pertechnetate will not complex with the most commonly used biological carriers for radionuclide tissue imaging. Thus, technetium-labelled imaging agents are generally prepared by admixing a pertechnetate-Tc99m isotonic saline solution, a technetium reductant (reducing agent) such as stannous chloride or sodium dithionite, and a chelate conjugated to the desired peptide carrier agent for targeting the organ of interest. Alternatively, an intermediate transfer liquid-technetium 99m complex may be prepared prior to addition to the chelate-biological molecule to maintain the oxidation state within a desired level. Examples of such include 99m Tc-tartrate or 99m Tc-gluconate.

Another problem is that technetium-containing scintigraphic imaging agents are known to be unstable in the presence of oxygen, primarily since oxidation of the reductant and/or the technetium -99m destroys the reduced technetium -99m/targeting carrier complex. Accordingly, such imaging agents are generally made oxygen-free by saturating the compositions with oxygen-free nitrogen gas or by preparing the agents in an oxygen-free atmosphere. Stabilization of imaging agents can also be achieved through chemical means. U.S. Pat. No. 4,232,000, Fawzi, issued Nov. 4, 1980, discloses the use of gentisyl alcohol as a stabilizer for technetium imaging agents. Similarly, U.S. Pat. No. 4,233,284, Fawzi, issued Nov. 11, 1980 discloses the use of gentisic acid as a stabilizer.

SUMMARY OF THE INVENTION

The present invention discloses novel radiolabelled peptide compounds, methods of preparing these compounds, pharmaceutical compositions comprising these compounds and the use of these compounds in kits for the therapeutic treatment of tumors and for diagnostic imaging of tumors. Certain tumors of endocrine-origin contain large numbers of receptors having a high affinity for somatostatin. Krenning, et al. (Lancet 8632, 242–244 (1989)). Examples of such tumors, having large numbers of high-affinity somatostatin receptors, are pituitary tumors, central nervous system tumors, breast tumors, gastro-entero-pancreatic tumors, small cell carcinoma of the lung, lymphomas, as well as their metastases.

In diagnostic tumor localization, a radiolabelled compound must be easily detectable and highly selective. High selectivity, which is essential in these compounds means that the diagnostic compound, after having been introduced into the body, accumulates to a greater degree in the target tissue or tissues, i.e. a malignant tumor, than in surrounding tissues. In using somatostatin or other such peptides as carrier agents in radiolabelled compounds, the specific high selectivity of the particular peptide used provides for the strong accumulation of the diagnostic/therapeutic compound in the target tissue or tissues, such as in tumors in the case of somatostatin, compared with the concentration thereof in non-target tissues. Additionally, therapeutic treatment of malignant tumors is achieved when radiolabelled peptide compounds are constructed using high energy Beta or Alpha emitting isotopes rather than the pure gamma emitters customarily used for diagnostic purposes.

The radiolabelled peptide compounds of the present invention employ the somatostatin peptide having sequence identification number 1:

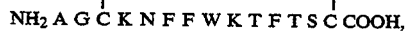

$NH_2$ A G C K N F F W K T F T S C COOH, wherein A represents Alanine, G represents Glycine, C represents Cysteine, K represents Lysine, N represents asparagine, F represents phenylalanine, W represents tryptophan, T represents threonine, and S represents serine, or a suitable derivative thereof.

In targeting particular receptors with radiolabelled somatostatin, it is not necessary that the complete fourteen (14) residue sequence of somatostatin be present. Binding is thought to reside primarily in the central core portion of the molecule, primarily, the phenylalanine-tryptophan-lysine-threonine or F W K T sequence. Through substitution in the somatostatin sequence, including some limited substitutions in the central core portion and perhaps incorporating (d) amino acid enantiomorphs, additional useful peptides are developed without affecting the binding specificity and affinity desired. Likewise peptidomimetic molecules may be prepared to duplicate this specific binding function. An example of such a useful peptide is SANDOSTATIN TM manufactured by SANDOZ Pharmaceuticals, Ltd., Basel Switzerland. The sequence of the Sandostatin TM peptide is:

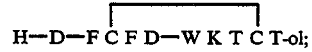

x $CH_3COOH$, wherein x equals 1.4 to 2.5.

In the present invention, the somatostatin peptide itself, or a molecule having somatostatin receptor specificity, may be radiolabelled using more than one method. The reaction generally takes place between the amino groups in the peptide and the carbonyl group in the active ester to form an amide bond. In particular, the peptides can be radiolabelled using either a conventional method referred to as "post-formed chelate approach" or by a recent method referred to as "pre-formed chelate approach" developed by Fritzberg et al., U.S. Pat. Nos. 4,965,392 and 5,037,630 incorporated herein by reference. In the "pre-formed approach," the desired ligand is complexed with the radionuclide and then conjugated to somatostatin or a molecule having somatostatin receptor specificity. In the "post-formed approach," the desired ligand is first conjugated to the peptide and the resulting conjugate is incubated with 99mTc sodium pertechnetate solution obtained from $^{99}Mo/^{99m}Tc$ generator along with a reducing agent. In the present invention, the latter approach has the additional advantage of allowing preparation of the complex in kit form. Users merely add $Na^{99m}TcO_4$ to the ligand-somatostatin conjugate or a derivative thereof for labelling to occur.

It is important to note a unique mechanism of the present invention whereby the conjugation reaction will only occur when the amino group is in the "free base" form, i.e., deprotonated to the $NH_2$ form. If the amino group is protonated, i.e., in the $NH_3^+$ form, the reaction will not occur. Therefore, in the molecules of the present invention it is important to perform the conjugation at neutral pH or within the range of 7.0 to 9.5 to avoid deprotonation of the epsilon-amino group of lysine, or K that is involved in binding. Avoiding the deprotonation of the epsilon-amino group involved in binding prevents the formation of a chelate complex which interferes with the binding site of the peptide and thus its ability to bind to the receptor. In the present invention, binding preferably occurs on the alpha amino group in order to avoid interference with the binding specificity of the somatostatin peptide.

Using either method of labelling the somatostatin peptide, any suitable ligand can be used to incorporate the preferred radionuclide metal ion such as technetium, rhenium, indium, gallium, samarium, holmium, yttrium, copper, or cobalt. The choice of the ligand entirely depends on the type of metal ion desired for diagnostic or therapeutic purposes. For example, if the radionuclide is a transition element such as technetium or rhenium, then ligands containing amine, amide, and thiols are preferred to form a stable complex whereas if the radionuclide is a lanthanide element, then polyaminocarboxyates or phenolate type ligands are preferable.

The above-described unique characteristics of the present invention make radiolabelled somatostatin and its derivatives very attractive for diagnostic purposes as well as for radiotherapy. The compounds of the present invention may be labelled with any radionuclide favorable for these purposes. Such suitable radionuclides for radiotherapy include but are not limited to Re-186, copper-67, Re-188 and cobalt-60. For diagnostic purposes the most suitable radionuclides include but are not limited to the transition metals as exemplified by technetium-99m and copper-62.

Due to the unique mechanism employed in the present invention to label the alpha amino group of somatostatin and avoid the epsilon amino group(s) (which would inhibit the ability of somatostatin peptides to bind to its receptor) a significantly advantageous radiolabelled peptide compound for radiotherapy and diagnostic imaging of tumors is achieved.

It is therefore an object of the present invention to provide a selective agent, both for the diagnostic imaging and for the therapeutic treatment of tumors containing high-affinity somatostatin receptors having a significantly high target to background ratio.

DETAILED DESCRIPTION OF THE INVENTION

The preferred peptide employed in the present invention is a somatostatin peptide or derivatives thereof as described in U.S. Pat. No. 4,395,403 incorporated herein by reference. The somatostatin peptide is radiolabelled using a pre-formed or post-formed methodology. In a preferred embodiment according to the present invention, the somatostatin or a molecule having somatostatin receptor specificity is first bonded to the $N_3S$ aminothiol ligand which is illustrated in FIG. 1

FIG. 1

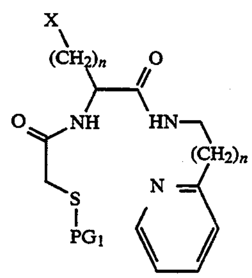

wherein m is a whole number less than eleven and preferably 3; p is either 0 or 1; $PG_1$ is a suitable sulfur protecting group selected from the group consisting of $C_{1-20}$ S-acyl such as alkanoyl, benzoyl and substituted benzoyl—whereby alkanoyl is preferable, $C_{1-20}$ S-acyl groups such as benzyl, t-butyl, trityl, 4-methoxybenzyl and 2,4-dimethoxybenzyl—whereby 2,4-dimethoxybenzyl is preferable, $C_{1-10}$ alkoxyalkyl such as methoxymethyl, ethoxyethyl and tetrahydropyranyl—whereby tetrahydropyranyl is preferable, carbamoyl, and $C_{1-10}$ alkoxy carbonyl such as t-butoxycarbonyl and methoxycarbonyl—whereby t-butoxycarbonyl is preferable; and X is a coupling moiety selected from the group consisting of carboxyl, amino, isocyanate, isothiocyanate, imidate, maleimide, chlorocarbonyl, chlorosulfonyl, succinimidyloxycarbonyl, haloacetyl and $C_{1-10}$ N-alkoxycarbamoyl—whereby N-methoxylcabamoyl is preferable.

In another preferred embodiment according to the present invention, somatostatin or a molecule having somatostatin receptor specificity is bonded to the $N_2S_2$ aminothiol ligand which is illustrated in FIG. 2;

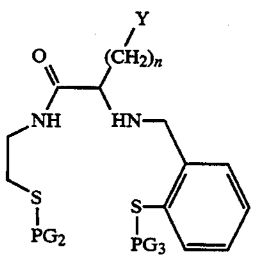

FIG. 2 wherein n is a whole number less than eleven and preferably 3; $PG_2$ and $PG_3$ may be the same or different sulfur protecting groups selected from the group consisting of $C_{1-20}$ S-acyl such as alkanoyl, benzoyl and substituted benzoyl—whereby alkanoyl is preferable, $C_{1-20}$ alkyl groups such as benzyl, t-butyl, 4-methoxybenzyl, trityl and 2,4-dimethoxybenzyl—whereby 2,4-dimethoxybenzyl is preferable, $C_{1-10}$ alkoxyalkyl such as for example methoxymethyl, ethoxyethyl, and tetrahydropyranyl—whereby tetrahydropyranyl is preferable, carbamoyl and $C_{1-10}$ alkoxycarbonyl such as methoxycarbonyl, ethoxycarbonyl and t-butoxycarbonyl—whereby t-butoxycarbonyl is preferable; and Y is a coupling moiety selected from the group consisting of carboxyl, amino, isocyanate, isothiocyanate, imidate, maleimide, chlorocarbonyl, chlorosulfonyl, succinimidyloxycarbonyl, haloacetyl, and $C_{1-10}$ N-alkoxycarbamoyl—whereby N-methoxylcabamoyl is preferable.

In another preferred embodiment of the present invention, somatostatin or a molecule having somatostatin receptor specificity is conjugated with the ligand illustrated in FIG. 3,

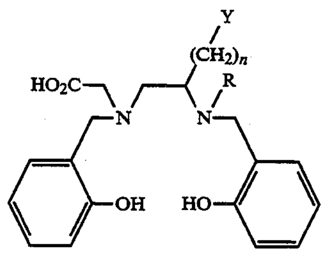

FIG. 3 wherein n varies from 1 to 10, and Y is a coupling moiety selected from the group consisting of carboxyl, amino, isocyanate, isothioganate, imidate, maleimide, chlorocarbonyl, chlorosulfonyl, succinimidyloxycarbonye, haloacetyl, and $C_{1-10}$ N-alkoxycarbamoyl such as N-methoxycarbamoyl and t-butoxycarbamonyl—whereby t-butoxycarbamonyl is preferable; and R is selected from the group consisting of hydrogen and $C_{1-10}$ alkyl such as methyl and t-butyl—whereby t-butyl is preferable.

In another preferred embodiment, the somatostatin or a molecule having somatostatin receptor specificity can be conjugated with the metal complex illustrated in FIG. 4

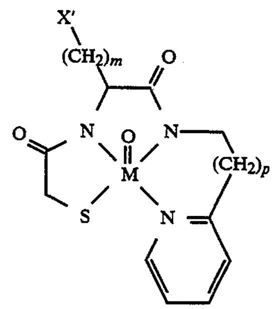

FIG. 4 wherein m is a whole number less than eleven and more preferably 3; p is either 0 or 1; X' is a coupling moiety selected from the group consisting of carboxyl, amino, isocyanate, isothiocyanate, imidate, maleimide, chlorocarbonyl, chlorosulfonyl, sucininimidyloxycarbonyl, haloacetyl and $C_{1-10}$ N-alkoxycarbamoyl such as N-methoxycarbamoyl and t-butoxycarbamoyl—whereby t-butoxycarbamoyl is preferable and M is a radionuclide suitable for diagnostic imaging or therapeutic use such as technetium, rhenium, copper, cobalt, indium, gallium, samarium, yttrium and holmium.

In another preferred embodiment, the somatostatin or a molecule having somatostatin receptor specificity can be conjugated with a metal complex as illustrated in FIG. 5 wherein Y' and n are defined the same respectively as Y and n in FIG. 3 and M is defined the same as M in FIG. 4.

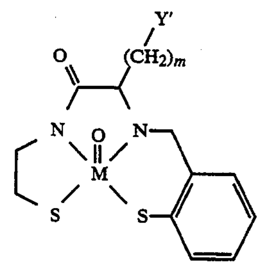

FIG. 5

In another preferred embodiment, the somatostatin or a molecule having somatostatin receptor specificity can be conjugated with a metal complex as shown in FIG. 6.

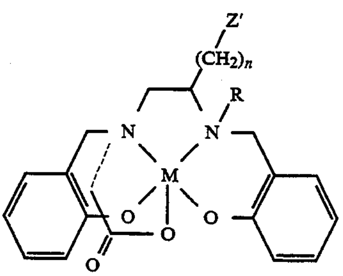

FIG. 6 wherein Z', q and R are defined the same respectively as Y, n and R of FIG. 3 and M is defined the same as M in FIG. 4.

In another preferred embodiment, the somatostatin or a molecule having somatostatin receptor specificity can be conjugated with a metal complex as shown in FIG. 7.

FIG. 7

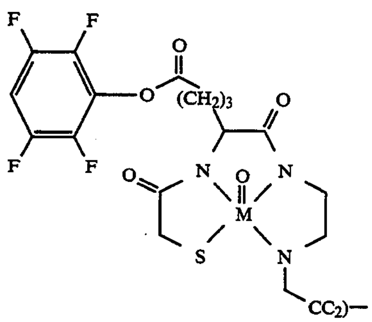

wherein M is defined the same as M in FIG. 4.

Common esters which have been found useful in this labelling technique are o- and p- nitrophenyl, 2-chloro-4-nitrophenyl, cyanomethyl, 2-mercaptopyridyl, hydroxybenztriazole, N-hydroxysuccinimide, trichlorophenyl, tetrafluorophenyl, thiophenyl, tetrafluorothiophenyl, o-nitro-p-sulfophenyl, N-hydroxyphthalimide and the like. For the most part, the esters will be formed from the reaction of the carboxylate with an activated phenol, particularly, nitro-activated phenols, or a cyclic compound based on hydroxylamine.

The advantages of using sulfur protecting groups include the fact that a separate step for removal of the sulfur-protective group is not necessary. The protecting groups are displaced from the compound during the labelling in what is believed to be a metal-assisted acid cleavage: i.e., the protective groups are displaced in the presence of a radionuclide at an acid pH and the radionuclide is bound by the chelating compound. The radiolabeling procedure thus is simplified, which is a significant advantage when the chelating compounds are to be radiolabelled in a hospital laboratory shortly before use. Additionally, another advantage of the present invention is that the basic pH conditions and harsh conditions associated with certain known radiolabeling procedures or procedures for removal of other sulfur protected groups are avoided. Thus, base-sensitive groups on the chelating compounds survive the radio-labelling step intact. Suitable sulfur-protecting groups, when taken together with the sulfur atom to be protected, include hemithioacetal groups such as ethoxyethyl, tetrahydrofuranyl, methoxymethyl, and tetrahydropyranyl. Other suitable sulfur protecting groups are $C_{1-20}$ acyl groups, preferably alkanoyl or benzoyl. Other possible formulas for the chelating compounds are described in the European Patent Application assigned publication number 0 284 071 incorporated herein by reference.

Synthesis of the Tc-99m bifunctional chelate and subsequent conjugation to a somatostatin peptide, or a derivative thereof, can be performed as described in the European Patent Application assigned publication number 0 284 071 and U.S. Pat. No. 4,965,392 incorporated herein by reference and related technologies as covered by U.S. Pat. Nos. 4,837,003, 4,732,974 and 4,659,839, each incorporated herein by reference.

After purification, technetium-99m labelled somatostatin peptide, or derivatives thereof, may be injected into a patient for diagnostic imaging or therapeutic use. The technetium-99m somatostatin compound is capable of reliably visualizing tumors within minutes of post-injection. The somatostatin peptide when radiolabelled with the technetium-99m triamide thiolate bifunctional chelate is efficacious as an in vivo diagnostic agent for the imaging of tumors of the type described above. The radiolabelled somatostatin compound of the present invention are described in still greater detail in the illustrative examples which follow.

EXAMPLE 1

A solution of somatostatin, or derivatives thereof, (0.01 mmol) in 2 mL of carbonate/bicarbonate buffer at pH 8.5±0.5 is treated with a solution of 0.1 mmol of the ligand in FIG. 1 (wherein m=2, p=1, $PG_1$ is benzoyl, and X is succinimidyloxycarbonyl) in dimethylformamide (0.5 mL) and the entire mixture is kept at room temperature for 2 hours. The mixture is then diluted with water (2.5 mL) and dialyzed extensively against water. After dialysis, the solution is lyophilized to give the desired somatostatin conjugate.

EXAMPLE 2

A solution of somatostatin, or derivatives thereof, (0.01 mmol) in 2 mL of carbonate/bicarbonate buffer at pH 8.5±0.5 is treated with a solution of 0.1 mmol of the ligand in FIG. 2 (wherein n=2, $PG_2$ and $PG_3$ are benzoyl, and Y is succinimidyloxycarbonyl) in dimethylformamide (0.5 mL) and the entire mixture is kept at room temperature for 2 hours. The mixture is then diluted with water (2.5 mL) and dialyzed extensively against water. After dialysis, the solution is lyophilized to give the desired somatostatin conjugate.

EXAMPLE 3

A solution of somatostatin, or derivatives thereof, (0.01 mmol) in 2 mL of carbonate/bicarbonate buffer at pH 8.5±0.5 is treated with a solution of 0.1 mmol of the ligand in FIG. 3 (wherein q=4, and Z is succinimidyloxycarbonyl) in dimethylformamide (0.5 mL) and the entire mixture is kept at room temperature for 2 hours. The mixture is then diluted with water (2.5 mL) and dialyzed extensively against water. After dialysis, the solution is lyophilized to give the desired somatostatin conjugate.

EXAMPLE 4

To 100 uL of a solution containing 5 mg of sodium gluconate and 0.1 mg of stannous chloride in water, 500 ul of 99m-Tc04 (pertechnetate) is added. After incubation at room temperature for about 10 minutes at room temperature, a solution of 500 uL of the somatostatin, or derivatives thereof, conjugates (1 mg/mL in 0.1M carbonate/bicarbonate buffer, pH 9.5) in Examples 1 or 2 is then added and the entire mixture is incubated at 37° C. for about 1 hour. The desired labelled peptide is separated from unreacted 99mTc-gluconate and other small molecular weight impurities by gel filtration chromatography (Sephadex G-50) using phosphine buffered physiological saline, (hereinafter PBS), 0.15M NaCl, pH 7.4 as eluent.

EXAMPLE 5

A mixture of gentisic acid (25 mg), inositol (10 mg), and the somatostatin, or derivatives thereof, conjugate (500 uL, 1 mg/mL in water) was treated with In-111 indium chloride in 0.05M HCl. The solution was allowed to incubate at room temperature for about 30 minutes. The desired labelled peptide is separated from unreacted In-111 indium salts and other small molecular weight impurities by gel filtration chromatography (Sephadex G-50) using phosphine buffered physiological saline, (PBS), 0.15M NaCl as eluent.

After the somatostatin or a derivative thereof is prepared and labelled according to the procedure described above, the compound is used with a pharmaceutically acceptable carrier in a method of performing a diagnostic imaging procedure using a gamma camera or like device. This procedure involves injecting or administering, for example in the form of an injectable liquid, to a warm-blooded animal an effective amount of the present invention and then exposing the warm-blooded animal to an imaging procedure using a suitable detector, e.g. a gamma camera. Images are obtained by recording emitted radiation of tissue or the pathological process in which the radioactive peptide has been incorporated, which in the present case are tumors, thereby imaging at least a portion of the body of the warm-blooded animal. Pharmaceutically acceptable carriers for either diagnostic or therapeutic use include those that are suitable for injection or administration such as aqueous buffer solutions, e.g. tris (hydroxymethyl-)aminomethane (and its salts), phosphate, citrate, bicarbonate, etc., sterile water for injection, physiological saline, and balanced ionic solutions containing chloride and/or bicarbonate salts of normal blood plasma cations such as $Ca^{2+}$, $Na^{+}$, $K^{+}$ and $Mg^{2+}$. Other buffer solutions are described in *Remington's Practice of Pharmacy*, 11th edition, for example on page 170. The carriers may contain a chelating agent, e.g. a small amount of ethylenediaminetetraacidic acid, calcium disodium salt, or other pharmaceutically acceptable chelating agents.

The concentration of labeled peptide and the pharmaceutically acceptable carrier, for example in an aqueous medium, varies with the particular field of use. A sufficient amount is present in the pharmaceutically acceptable carrier in the present invention when satisfactory visualization of the tumor is achievable or therapeutic results are achievable.

The composition is administered to the warm-blooded animals so that the composition remains in the living animal for about six to seven hours, although shorter and longer residence periods are normally acceptable.

The radiolabelled somatostatin compounds of the present invention or somatostatin derivatives thereof, prepared as described herein, provide means of in vivo diagnostic imaging of tumors or therapeutic treatment of tumors which provides many advantages over prior known procedures for targeting the particular tumors of choice.

After consideration of the above specification, it will be appreciated that many improvements and modifications in the details may be made without departing from the spirit and scope of the invention. It is to be understood, therefore, that the invention is in no way limited, except as defined by the appended claims.

We claim:

1. A composition comprising somatostatin or a peptide which retains somatostatin receptor specificity conjugated with a $N_3S$ ligand having the general structure

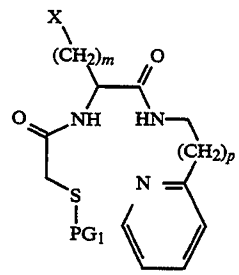

wherein m is a whole number less than eleven; p is either 0 or 1; $PG_1$ is a sulfur protecting group selected from the group consisting of $C_{1-20}$ S-acyl, $C_{1-20}$ alkyl, $C_{1-10}$ alkoxyalkyl, carbamoyl and $C_{1-10}$ alkoxycarbonyl and X is a coupling moiety selected from the group consisting of carboxyl, amino, isocyanate, isothiocyanate, imidate, maleimide, chlorocarbonyl, chlorosulfonyl, succinimidyloxycarbonyl, haloacetyl and $C_{1-10}$ N-alkoxycarbamoyl.

2. The composition of claim 1 labelled in a $^{99m}$Tc-pertechnetate solution containing a reducing agent, a buffering agent, and a transfer ligand such as sodium gluconate or tartarate.

3. The composition of claim 1 labelled in a 186/188 Re-perrhenate solution containing a reducing agent, a buffering agent, and a transfer ligand such as sodium gluconate or tartarate.

4. A composition comprising somatostatin or a somatostatin derivative having somatostatin receptor specificity conjugated with a metal complex having the general structure

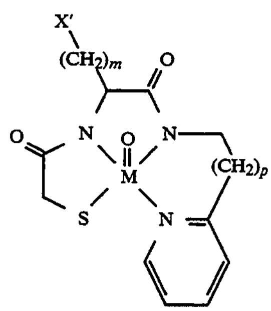

wherein m is a whole number less than eleven; p is either 0 or 1; X' is a coupling moiety selected from the group consisting of carboxyl, amino, isocyanate, isothiocyanate, imidate, maleimide, chlorocarbonyl, chlorosulfonyl, succinimidyloxycarbonyl, haloacetyl and $C_{1-10}$ N-alkoxycarbamoyl; and M is technetium, rhenium, gallium, copper or cobalt.

5. The composition of claim 4 labelled in a $^{99m}$Tc-pertechnetate solution containing a reducing agent, a buffering agent, and a transfer ligand such as sodium gluconate or tartarate.

6. The composition of claim 4 labelled in a 186/188 Re-perrhenate solution containing a reducing agent, a buffering agent, and a transfer ligand such as sodium gluconate or tartarate.

7. The composition of claim 4, wherein M is $^{99m}$technetium.

8. The composition of claim 4, wherein M is rhenium-186 or rhenium-188.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 14 amino acids
( B ) TYPE: amino acid
( C ) TOPOLOGY: linear ( i i ) MOLECULE TYPE: protein ( i i i ) HYPOTHETICAL: NO ( v i ) ORIGINAL SOURCE:
( A ) ORGANISM: Somatostatin
( B ) STRAIN: Human ( x i ) SEQUENCE DESCRIPTION: SEQ ID NO: 1:

```
Ala Gly Cys Lys Asn Phe Phe Trp Lys Thr Phe Thr Ser Cys
1               5                   10
```